United States Patent
Hoult

(10) Patent No.: US 6,518,573 B1
(45) Date of Patent: Feb. 11, 2003

(54) SUPPRESSION OF UNDESIRED COMPONENTS IN THE MEASURED SPECTRA OF SPECTROMETERS

(75) Inventor: Robert Alan Hoult, Buckinghamshire (GB)

(73) Assignee: Wellesley International C.V. (CH)

( * ) Notice: Subject to any disclaimer, the term of this patent is extended or adjusted under 35 U.S.C. 154(b) by 0 days.

(21) Appl. No.: 09/383,242

(22) Filed: Aug. 26, 1999

(30) Foreign Application Priority Data

Aug. 28, 1998 (EP) .............................................. 98306929

(51) Int. Cl.$^7$ .............................................. G01N 21/35
(52) U.S. Cl. .................................................. 250/339.09
(58) Field of Search .................................... 250/339.09

(56) References Cited

U.S. PATENT DOCUMENTS

| | | |
|---|---|---|
| 5,121,337 A | 6/1992 | Brown |
| 5,299,138 A | 3/1994 | Fiori et al. |
| 5,596,992 A | 1/1997 | Haaland et al. |
| 5,760,785 A | 6/1998 | Barber et al. .............. 345/440 |

FOREIGN PATENT DOCUMENTS

WO 9207275 4/1992 ............ G01R/7/10

OTHER PUBLICATIONS

Véronique Carrére, "Effects of Change in Spectral Resolution and Channel Position on Radiative Transfer Model–based Atmospheric Correction Techniques Applied to Imaging Spectrometers." *Geoscience and Remote Sensing Symposium, 1994. IGARASS '94. Surface and Atmospheric Remote Sensing: Technologies, Data Analysis and Interpretation., International.* vol. 1, pp. : 47–49, Aug. 8–12, 1994.*

* cited by examiner

*Primary Examiner*—Constantine Hannaher
(74) *Attorney, Agent, or Firm*—St. Onge Steward Johnston & Reens LLC

(57) ABSTRACT

The effects of unwanted components such as $H_2O$ and $CO_2$ in spectral data measured by a spectrometer such as an FT-IR spectrometer are suppressed by a technique in which data representing high resolution spectra of the unwanted component is acquired, this data is modified so that its resolution matches that of the instrument, the results data is filtered to allow for perturbing effects of the sample and the resulting data is subtracted from the measured sample spectrum to provide corrected output data.

16 Claims, 3 Drawing Sheets

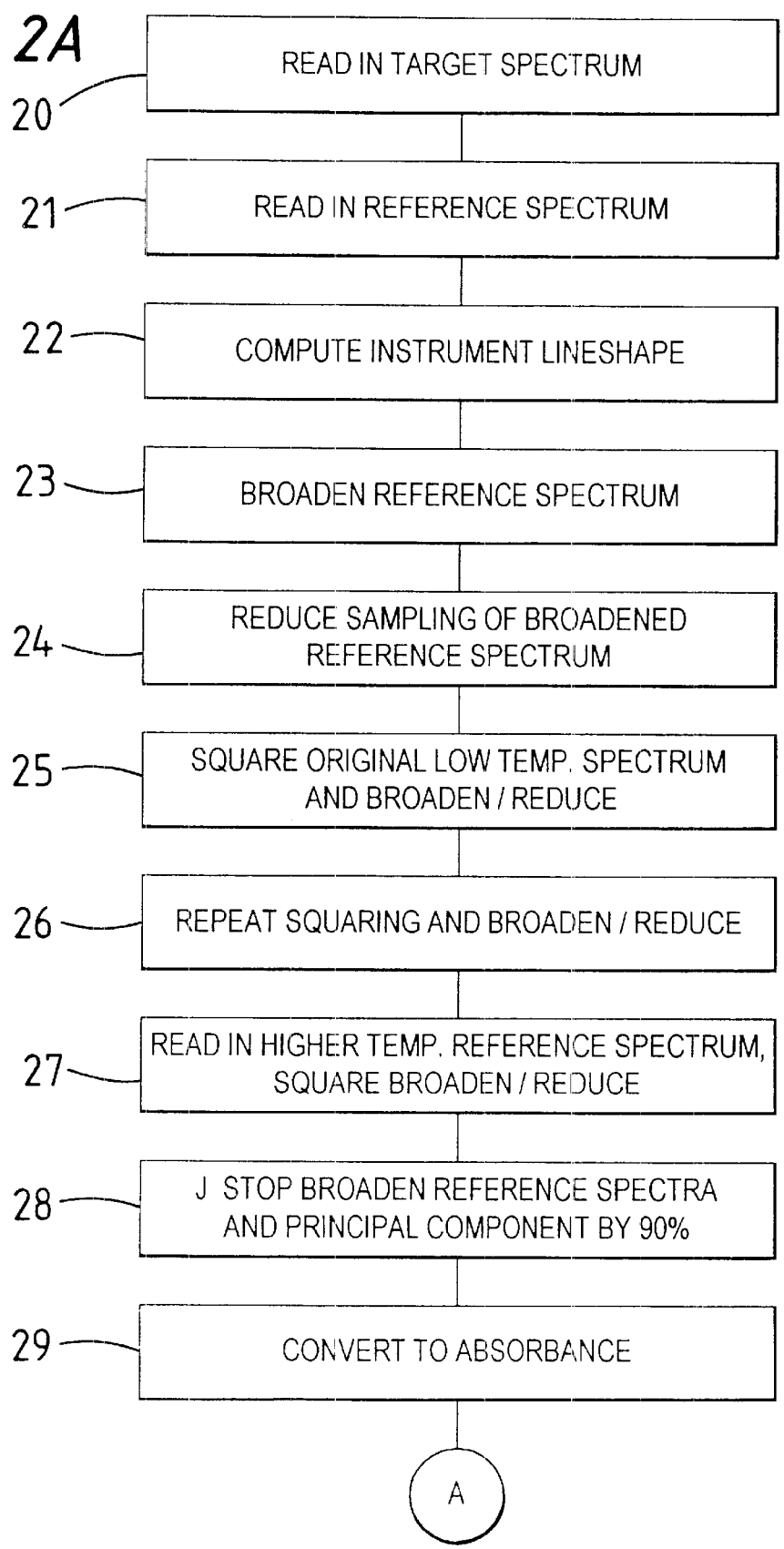

SUPPRESSION OF UNDESIRED COMPONENTS IN THE MEASURED SPECTRA OF SPECTROMETERS

FIELD OF THE INVENTION

This invention relates to spectrometers and in particular relates to suppressing undesired spectral components in the spectra obtained from the spectrometers. The invention has particularly but not exclusive application to FT-IR spectroscopy.

BACKGROUND ART

In for example an FT-IR spectrometer, infra-red or near infra-red radiation is directed from a source of such radiation towards a sample under investigation. Radiation transmitted by or reflected from the sample is received at a detector or receiver and the output of the detector is processed by a signal processor in order to obtain the spectral characteristics of the sample. In carrying out measurements it is first necessary to obtain what is known as a background measurement that is to say to measure the background spectrum without a sample in place at the sample station. Subsequently measurements are made with the sample in place and the desired sample spectrum is obtained from the ratio of the measurement obtained with the sample in place to the background measurement.

A significant proportion of Spectroscopy performed in the mid infra-red range is concerned with spectra of solids and liquids which have absorbtion bandwidths in the tens of wave numbers. As a consequence, many of the measurements are made at, for example, 4 cm−1 or 2 cm−1 resolution. At such moderate resolutions water vapour having line widths closer to 0.1 cm−1 is strongly under resolved and bands that might otherwise be saturated with absorbance well in excess of 1.0 are broadened to the point where they show relatively low peak absorbance. Two major consequences result from this under resolution: The absorbance becomes substantially non-linear with concentration causing the absorbance spectrum shape to become a strong function of concentration and in additional the lineshapes become entirely dominated by the instrument lineshape function making the spectra have a different character according to the instrument type and set up. More significantly since the instrument lineshape function may well be influenced by the sample or sampling accessory through vignetting another beamed geometry disturbances the water vapour spectrum in the sample spectrum may not entirely resemble the nominally similar spectrum in the background That is to say the effects do not cancel out when the sample spectra and the background spectra are ratioed. The overall result is that it is extremely difficult to subtract out the effects of water vapour consistently by any means of linear spectrum differencing typically employed. A similar problem exists with .other unwanted components such as those of carbon dioxide.

A further aspect of the problem is related to the overlap of features in the sample spectrum with features in the water vapour spectrum. Even when an exact spectrum of water vapour measured under the current sampling conditions can be generated independently by some means, it is very difficult to estimate precisely the proportion of water vapour spectrum that must be subtracted out from the detected spectra especially by automatic algorithmic approaches.

SUMMARY OF THE INVENTION

The present invention is concerned with a novel technique for subtracting out from the measured sample spectrum undesired components such as those arising from water vapour and carbon dioxide.

According to the present invention there is provided a spectrometer which comprises a source of analysing radiation, a detector for detecting radiation transmitted through or reflected from a sample under investigation, and a processing means for processing the output of the detector to produce spectral data relating to a sample under investigation, wherein the processor is arranged, in order to suppress the effects of unrequired components such as water vapour or carbon dioxide in the spectral data, to acquire reference data representing high resolution spectra of the unwanted component or components, to modify said data so that its resolution simulates that of the spectrometer, to filter said data so as to allow for pertutbing effects in the sample spectrum and to subtract the resulting data from the measured sample spectrum in order to provide a corrected output data. The acquired data may represent said high resolution spectra at a plurality of temperatures. The modification may comprise processing said reference data so as to broaden the resolution to that which matches the sample spectral data being measured. The broadening may be carried out by a convolution technique in which the reference data are convolved with a computed line shape function appropriate to the spectrometer. These steps may be repeated for different reference data representing different concentrations of unwanted component or components.

The processor may also be arranged to generate perturbed versions of the broadened reference data to take into account variations in at least some operating parameters such as temperature and optical line width.

The filtering may include creating a filter for filtering the spectra to emphasise higher resolution parts of the unrequired components. The filter may comprise a band pass filter. Filtering may also include carrying out a least square fit of the filtered sample spectral data to the filtered unwanted component spectra. Additionally the processor may iterate the least square fit to remove those parts of the spectrum which have a poor fit.

The processor may be arranged to use the resulting co-efficients to compute an unfiltered unwanted component spectrum. This is then subtracted from the measured sample spectrum in order to obtain a corrected sample spectrum.

BRIEF DESCRIPTION OF THE DRAWINGS

The invention will now be described now by way of example and with particular reference to the accompanying drawings. In the drawings.

DETAILED DESCRIPTION OF THE PREFERRED EMBODIMENT

Figure 1:
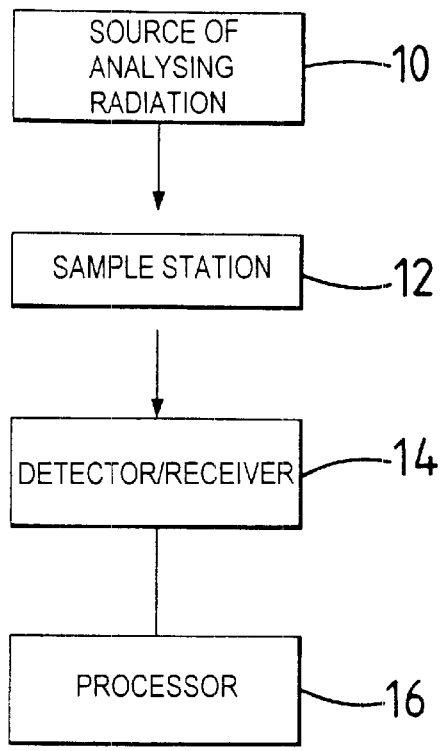
FIG. 1 is a schematic illustration of an infrared spectrometer in which the present technique can be implemented and FIG. 2 is a flow chart illustrating the sequence of steps carried out by a processor arranged to operate in accordance with the present invention.

Referring to FIG. 1 of the drawings an infrared spectrometer of the single beam type such as an FT-IR spectrometer in very general terms, comprises a source of analysing radiation 10 which is arranged to direct analysing radiation to a sample station 12. Typically the source of analysing radiation will be associated with an interferometer of the Michelson type which produces a scanning beam by means of which the sample can be irradiated. Radiation from the sample station 12 is received at a detector or receiver 14 and the output of the receiver is processed by a processor 16 to provide data representative or the spectrum of a sample under investigation. Generally speaking a spectrometer of this type has an associated PC for carrying out at least some of the processing and enabling an operator to issue appropriate instructions to operate the spectrometer. The way in which a spectrometer of the type shown in FIG. 1 operates in order to obtain a spectrum will be known to those skilled in the art and will therefore not be described in any more detail since it is unnecessary for understanding the present invention.

Embodiments in accordance with the present invention are concerned with routines which are operated by the processor in order to suppress or cancel out the effects of undesired components such as water vapour or carbon dioxide in the measured sample spectra. It is envisaged that such routines can be operated by a wide range of spectrometers provided that the processing means of the spectrometer has sufficient capability to run the software involved in carrying out the routines. The description given here is directed in the main to the way in which the invention can be implemented in FT-IR spectroscopy.

Initially a general description of the method will be given followed by an implementation in more specific terms. The description will refer to removing the effects of water vapour but it should be understood that the technique applies equally well to suppression of other undesired components such as carbon dioxide.

In very general terms the processor is arranged to remove or suppress the effects of any water vapour components in the spectrum by the following steps.

1. Generating a properly broadened approximately representative set of spectra for the unwanted component which span the range of non-linear behaviour expected in the instrument.
2. Generating perturbed spectra to take into account a degree of variability in lineshape parameters; and
3. Iterative fitting using a combination of filtering techniques.

The initial step in the method is to acquire stored high resolution spectral data relating to water vapour. This should have sufficient resolution to accurately characterize the natural lineshape. It is only when the line shape is properly resolved that the behaviour of the bands can be properly represented as peak absorbances increase and the non-linearity of the transmission values becomes significant. Such data is available commercially and one example which can be used is a set of peak tables known as (HITRAN). Significant parameters of such spectral data are atmospheric pressure which under normal circumstances is responsible for line broadening and in the present case will be understood to be one atmosphere, and a representative gas temperature which in the present case is taken to be 23° C., a typical laboratory environment.

Starting from this single spectrum the method generates spectra for three different concentrations of water at a pathlength typical of the actual pathlength encountered in practice eg 25 cm. The concentrations selected are 25% relative humidity, (RH) 50% RH and 100% RH thereby spanning the range of concentrations typically encountered in practice. The simple way of obtaining these spectra is to square the transmittance spectrum of a base 25% RH spectrum to obtain the 50% RH spectrum and then repeat the process in order to obtain the 100%RH spectrum. An alternative way of doing this would be by a conventional logarithmic scaling technique.

These three principal spectra are then broadened in transmittances in order to simulate approximately the broadening that occurs in the spectrometer itself. In the present case, ie a Fourier Transform spectrometer, the spectrum is broadened on a linear wave number abscissa using an FT lineshape function arising from a combination of the interferogram scan length used in the instrument and an apodisation function employed. The broadening can be performed either in spectrum space with a convolution or interferogram space by multiplying an envelope function. In the present example the operation is carried out in the spectrum space. In the next step the spectrum is broadened on a logarithmic wave number abscissa using a rectangular line shape function associated with a perfectly behaved circular Jacquinot stop. The Jacquinot stop controls the divergence of rays passing through the interferometer of the spectrometer and effectively controls its resolving power. The associated line width is proportional to wave number and hence on a logarithmic scale appears to have constant width. There are a number of ways in which this calculation can be performed. In the present case it is achieved by computing the mean value over the line width from the area under spectrum, using a variable line width. It should be understood that the Jacquinot stop can also introduce a spectrum shift. In the present case this is already substantially calibrated out by use of a centre broadening function.

At this stage the process has produced three principal broadened spectra at the various concentrations. The next step is to generate three additional minor components which allow for variation from the computed spectra. The first is a similarly broadened spectrum at 50% RH but at 10° C. higher temperature to allow for temperature variation. The second is at 50% RH at the standard temperature broadened with a slightly smaller Jacquinot stop function to allow for imperfect optics. The third is a spectrum shifted in wave number by a small constant to allow for calibration errors. In each case, the minor component actually employed in the subsequent processing is the difference between the perturbed spectrum and the principal 50% RH component.

In the majority of cases the six components that it is to say the three major components and the three minor components should be sufficient to implement a technique in accordance with the present invention. However, if necessary it would be possible to iterate the fit using more appropriate starting parameters once estimates for the parameters have been made from the fit components, for example temperature and path length. In some cases it may be possible to operate with less than six components especially if an iterative approach of refining the initial parameter estimates is adopted. An iterative approach works best for single beam spectra where the water vapour spectrum is directly represented as opposed to a ratio spectrum where only small differences in water vapour may be present. Once having refined the parameters from the single beam subsequent elimination of the effects of water vapour is best carried out on the ratio spectrum since the ration itself eliminates a significant part of the water vapour effect.

Having established the components which can be used to accurately reconstruct the expected water vapour transmittance spectrum, it is necessary to determine the proper coefficients for the fit in the presence of the unknown and potentially significant determining factors in the data arising from, for example, the spectrum of the sample. These may be many times stronger that the spectrum of the water vapour. It is found in practice that the problem of subtracting out the water vapour remains linear in absorbance even though the construction of the water vapour spectrum itself is a non-linear problem. Thus, in the present example the spectra are converted to absorbance before the following operations.

The first step in reducing the interference from the sample spectra is to filter all the data, that is the calculated component spectra and the sample spectrum, with a band pass filter that accepts data centred around 10 cm−1 resolution while rejecting data at higher and particularly lower resolution. The parameters of this filter are based on the general properties of infra-red spectra of solids and liquids typically measured in the applications of concern. The underlying principle is that of a matched filter.

In order to create such a filter typical sample spectra obtained from a commercial library are Fourier transformed and the square root sum of squares of the real and imaginary components calculated in order to give an idea of the distribution of the information present across the range of resolution. In the present case this indicates the amount of data at resolutions better than 10 cm−1 is relatively small. A similar calculation for water vapour shows that being a gas there is considerable information up to the resolution limit of the spectrum. The ratio of the data for the water vapour versus the library data shows a broad peak centred around 10 cm−1. The shape of this peak approximates to a gaussian and this function forms the basis of the matched filter, and is analytic in both transform spaces.

It should be noted that the matching of the filter is not especially critical and good results can be obtained using a simple first derivative filter. However, a gaussian function approximates closely to the ideal for a general case.

The above described resolution filtering reduces the effects of interference to water vapour least square fits significantly. However, it is still not sufficient to produce a satisfactory result in many situations. In order to achieve this an additional step of iterative weighting of the fit in the spectrum domain is carried out.

In this the initial weight function employed is the measured transmittance spectrum itself. The reason for this is that regions of low transmittance have poor signal to noise ratio and a good fit cannot be expected in these regions. The weighted least squares fit of the filtered data is computed and the residual spectrum calculated. The weighted root mean square residual value is calculated and then the weight function is modified to set zero weight for those portions of the spectrum where the residue exceeds four times the rms value. This process effectively blanks out regions of the spectrum where the fit is particularly bad. The fit is iterated and the process repeated until the fit is sufficiently improved. There may be a compromise between the number of iterations and the severity of the blanking and in practice it is found that the final result is better with less severe blanking and more iterations.

Having calculated the best parameters of the fit using filtered data the process reconstructs the full water vapour spectrum using the same fit parameters with the unfiltered data. The measured sample spectrum is then divided in transmittance by the water vapour spectra in order to eliminate the water vapour component.

It is believed that the above description will enable a reasonably competent computer programmer to implement a program for carrying out the process described.

Figure 2C:
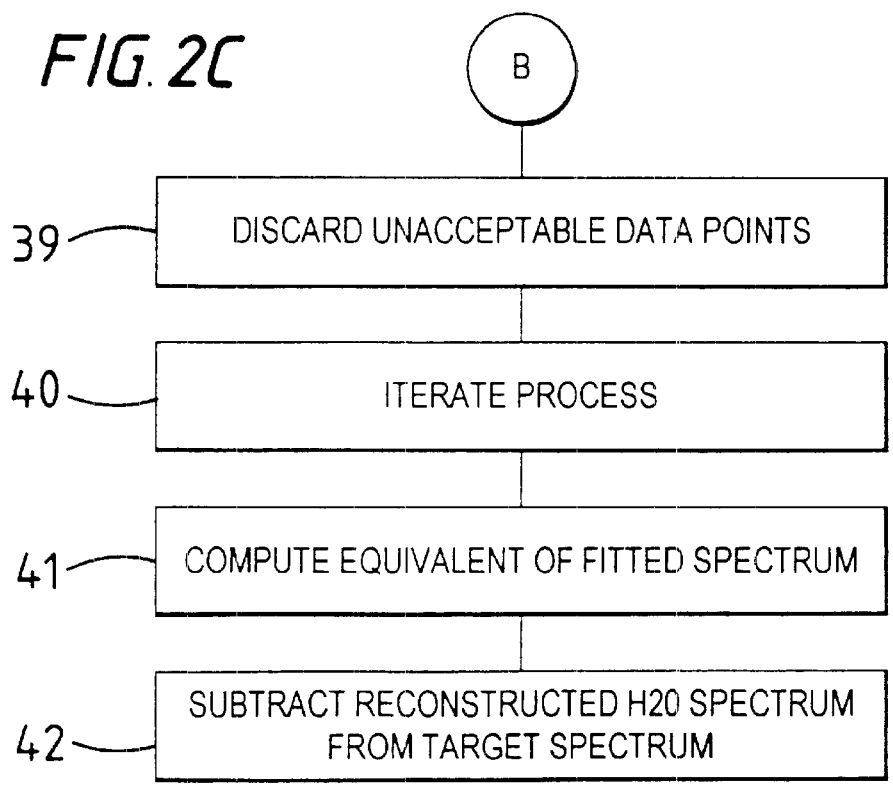
Figure 2B:
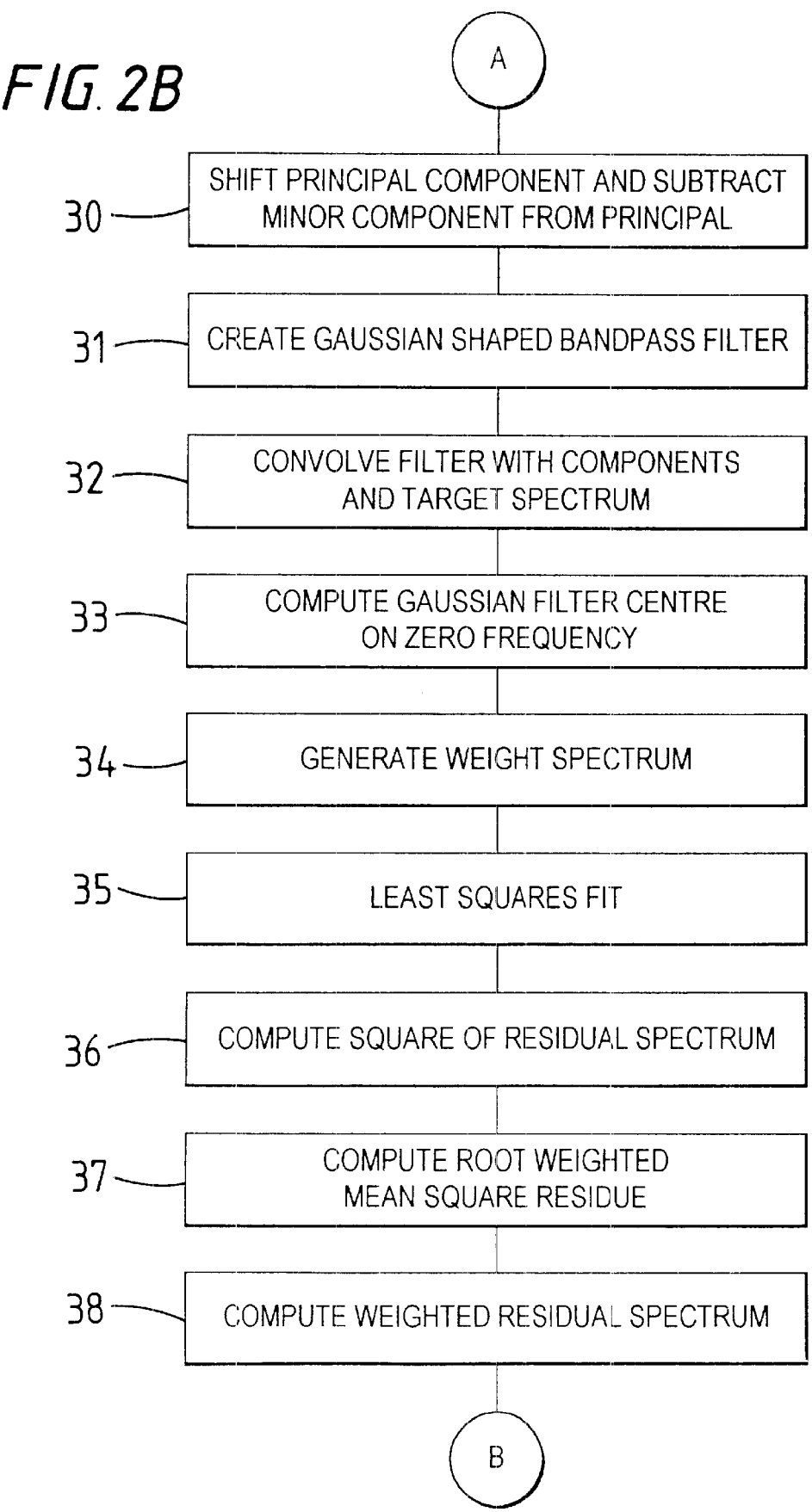

In order to assist in this respect the following description in conjunction with the flow chart of FIG. 2 is included as a specific example for eliminating an unwanted component in accordance with the present invention.

This program effectively has two inputs these being as follows:

1 The first is the target spectrum or the measured spectrum of the sample from which the water vapour component is to be subtracted. The spectrum is typically a low resolution spectrum measured at around 4 cm−1 resolution in transmittance, digitised at a constant wave number interval at around 2×over-sampling, that is at 1 cm−1 interval.

2 This is the high resolution reference spectra of water vapour at two different temperatures. These spectra typically resolve the natural line width of the water vapour under measurement conditions of the target spectrum, ie around 0.1 cm−1 for normal pressure, and are stored in transmittance Eat intervals of ¹⁄₆₄ cm−1. The two temperatures should lie on either side of the temperature of the target spectrum and the water vapour concentration should be set around 25% RH at the path length of the target spectrum.

Referring now to FIG. 2 the first step illustrated at 20 is the reading of the target spectrum that is to say the spectrum measured by the spectrometer. The next step illustrated at 21 is to read in the lower temperature reference spectrum, ie the second input referred to above.

The next step shown at block 22 is to compute the lineshape corresponding to the Fourier transform by which the target spectrum was generated. This line shape is calculated by computing either analytically or numerically the Fourier transform of the apodisation function applied to the interferogram from which the target spectrum was generated. In the case of no apodisation the lineshape will be a sinc function of an appropriate width.

The next step shown at block 23 is to broaden the reference spectrum to the same nominal resolution as the target spectrum by convolving with the computed lineshape. Convolving involves multiplying the first part of the reference spectrum by a short line function and summing the products. Then the alignment of the two spectra is shifted along by one point and the process repeated. The sums form a new spectrum which is the convolution of the original spectrum with the lineshape function.

The next step is to reduce the sampling of the broaden reference spectrum to the same interval as the target spectrum by dropping data points. It should be noted that once the lineshape has been broadened data points can be discarded without loss of information.

The next step, as illustrated at 25, is to square the original low temperature reference spectrum to produce a 50% RH spectrum and this is broadened in a manner similar to that described for the initial reference data.

Referring to block 26 this is then repeated to give the 100% RH broadened reference spectrum. At this stage there exist three spectra for that cover the concentration range of the target spectrum. The 50% RH spectrum will be referred to as the principal component.

The next step as illustrated at 27 is to read in the higher temperature reference spectrum. This is squared and broadened in a manner similar to that already described to a give a broadened 50% RH higher temperature fourth component. This will be used later to allow for any temperature variation in the target spectrum. Each of the four components are then further broadened by a rectangular shape function which represents the ideal effect of the spectrometers optical aperture. This rectangular function has a theoretical fractional optical frequency width dnu/nu=1−cos(theta) where that is the semi-angle subtended by the Jacquinot stop aperture at the collimating mirror.

$$\text{Theta=arctan (j-stop diameter/2*focal length)}$$

The convolution is computed directly by numerical integration of the area under this rectangle when multiplied into the operand spectrum.

At this stage the process has computed four of the six required component spectra. The next step is to generate in a similar manner a j-stop broadened version of the principal component but with 10% narrower rectangular functions. This allows for some experimental variability of optical line width.

The principal component is then interpolated to generate a sixth component with a small wave number shift proportional to optical frequency. This allows for some tolerance in the frequency calibration of the target.

Then all six components are converted to absorbance as illustrated at block 30 and the principal component subtracted from the last three so that the process handles only minor perturbations produced by temperature, j-stop and shift.

The next step, shown in 31 is to produce a guassian-shaped band pass digital filter function of width (1/e) of 0.25 the Nyquist frequency and centred at 0.25 the Nyquist frequency. This filter can be generated analytically and serves to emphasize high resolution information unique to the water vapour spectrum. In the next step 32 this filter is convolved with all components and also with the target spectrum. Then a gaussian filter is computed which has a similar width which is centred at zero frequency (33). This filter is convolved with the unfiltered principal component to generate a weight spectrum (34) The filter so generated effectively smooths the absorbance peaks of the water vapour spectrum to generate a function that resembles the envelope of the peaks. The weight function is further multiplied by the unfiltered transmittance target spectrum.

The next step illustrated at 35 is to carry out a least squares fit of the six filtered components to the filtered target data using the weights. This composite weight function ensures closeness of fat wherever the water vapour is likely to be most intrusive.

The next step shown by block 36 is to compute the square of the residual spectrum multiplied by the weight spectrum. The residual spectrum is the difference between the target and the fitted spectrum. The fitted spectrum is computed by summing the component spectra scaled by the coefficients derived in the least squares fitting process.

Referring to block 37 the next step is to compute the root weighted mean square residue. This number is the analog of the rms residue in an unweighted fit.

Then the process computes a weighted residual spectrum as illustrated at block 38 and then identifies data points in the weighted residual spectrum which are greater than 4×the root weighted mean square residue and zeros the corresponding weights in the weighting spectrum. This process identifies data points in the target that are beyond the acceptable range and discards them as illustrated at 39.

The process is then iterated (40) from the least square fit step typically six times in order to refine the fit and to make sure that the majority of the unacceptable data has been removed.

The process then uses the fit coefficients generated in the final iteration to compute an equivalent of the fitted spectrum from the unweighted unfiltered components. (See block 41.)

This reconstructed water vapour spectrum is then subtracted from the unfiltered target spectrum (42). The reconstructed spectrum should accurately match the water vapour component in the target spectrum which should then subtract out cleanly. The result is the sample spectrum without the water vapour component.

By way of general comments the effects of water vapour are most prominent in well separated spectrum regions for example the regions centred around 1600 cm−1 and the region around 3700 cm−1. In theory since these are all part of the same water vapour spectrum, one set of fit parameters should suffice for all regions. However modelling in such well separated spectrum regions may not be exact and it may be necessary to treat the regions independently.

At higher optical frequencies the instrument line shape function can become increasingly dominated by geometric and optical factors in the beam path. The method described above relies for its basis spectra on a reasonably close approximation to ideal behaviour since the Jacquinot stop is assumed to give rise to a rectangular line shape. Although the fit is not particularly sensitive to exact details of this line shape, being dominated for the most part by FT line shape, it may be preferable in some situations to use an alternative broadening function for the Jacquinot stop effect.

The parameters of the least squares fit can yield diagnostic information on instrument performance. For example the overall strength of the water bands in the background spectrum can be used to indicate the state of purge of the instrument, the amount of shifted spectrum employed in the fit can be used as a check on the abscissa calibration. It could in principle be used as the primary abscissa calibration, although this may not be wholly desirable.

The method described above relates to suppression of water vapour components. The principles described can be applied equally well to removal of carbon dioxide components. However, account needs to be taken of differences arising from the difference in spectrum and resolution distribution. Carbon dioxide has a more regular band strength structure that is easily obscured by underresolving but on the other hand it has less overlap with typical sample spectra, particularly in the strong 2350 cm−1 band. This tends to place more emphasis on the spectrum weighting and less on resolution filtering.

What is claimed is:

1. A spectrometer which comprises a source of analyzing radiation, a detector for detecting radiation transmitted through or reflected from a sample under investigation, and a processor for processing the output of the detector to produce spectral data relating to the sample under investigation, wherein the processor is arranged, in order to suppress the effects of carbon dioxide in the spectral data, to acquire reference data representing high resolution spectra of the carbon dioxide, to modify said reference data so that its resolution simulates that of the spectrometer, to filter said reference data so as to allow for perturbing effects in the sample spectrum and thereby produce filtered data and to subtract the filtered data from the spectral data relating to the sample under investigation in order to provide a corrected output data.

2. A method of operating a spectrometer which comprises a source of analyzing radiation, a detector for detecting radiation transmitted through or reflected from a sample under investigation, and a processor for processing the output of the detector to produce spectral data relating to the sample under investigation, said method being carried out in order to suppress the effects of carbon dioxide in the spectral data, and comprising the steps of acquiring reference data representing high resolution spectra of the carbon dioxide, modifying said reference data so that its resolution simulates that of the spectrometer, filtering said reference data so as to allow for perturbing effects in the sample spectrum and thereby produce filtered data and subtracting the filtered data from the spectral data relating to the sample under investigation in order to provide a corrected output data.

3. A spectrometer which comprises a source of analyzing radiation, a detector for detecting radiation transmitted through or reflected from a sample under investigation, and a processor for processing the output of the detector to produce spectral data relating to the sample under investigation, wherein the processor is arranged, in order to suppress the effects of at least one unwanted component in the spectral data, to acquire reference data representing high resolution spectra of the at least one unwanted component at a plurality of temperatures, to modify said reference data so that its resolution simulates that of the spectrometer, to filter said reference data so as to allow for perturbing effects in the sample spectrum and thereby produce filtered data and to subtract the filtered data from the spectral data relating to the sample under investigation in order to provide a corrected output data.

4. A spectrometer which comprises a source of analyzing radiation, a detector for detecting radiation transmitted through or reflected from a sample under investigation, and a processor for processing the output of the detector to produce spectral data relating to the sample under investigation, wherein the processor is arranged, in order to suppress the effects of at least one unwanted component in the spectral data, to acquire reference data representing high resolution spectra of the at least one unwanted component, to modify said reference data so that its resolution simulates that of the spectrometer, to filter said reference data so as to allow for perturbing effects in the sample spectrum and thereby produce filtered data and to subtract the filtered data from the spectral data relating to the sample under investigation in order to provide a corrected output data, wherein the processor is further arranged to generate perturbed versions of the broadened reference data, to take into account variations in at least some operating parameters such as temperature and optical line width.

5. A spectrometer which comprises a source of analyzing radiation, a detector for detecting radiation transmitted through or reflected from a sample under investigation, and a processor for processing the output of the detector to produce spectral data relating to the sample under investigation, wherein the processor is arranged, in order to suppress the effects of at least one unwanted component in the spectral data, to acquire reference data representing high resolution spectra of the at least one unwanted component, to modify said reference data so that its resolution simulates that of the spectrometer, to filter said reference data so as to allow for perturbing effects in the sample spectrum and thereby produce filtered data, wherein the filtering includes creating a filter for filtering the reference data to emphasise the high resolution spectra of the at least one unwanted component, and to subtract the filtered data from the spectral data relating to the sample under investigation in order to provide a corrected output data.

6. A spectrometer according to claim 5 wherein the filter comprises a band pass filter.

7. A spectrometer according to claim 6 wherein the filtering also includes carrying out a least square fit of the filtered sample spectral data to the filtered unwanted component spectra.

8. A spectrometer according to claim 7 wherein the processor is also arranged to iterate the least square fit to remove those parts of the spectrum which have a poor fit.

9. A spectrometer according to claim 7 wherein the processor is arranged to use the resulting coefficients to compute an unfiltered unwanted component spectrum.

10. A method of operating a spectrometer which comprises a source of analyzing radiation, a detector for detecting radiation transmitted through or reflected from a sample under investigation, and a processor for processing the output of the detector to produce spectral data relating to the sample under investigation, said method being carried out in order to suppress the effects of at least one unwanted component in the spectral data and comprising the steps of acquiring reference data representing high resolution spectra of the at least one unwanted component at a plurality of temperatures, modifying said reference data so that its resolution simulates that of the spectrometer, filtering said reference data so as to allow for perturbing effects in the sample spectrum and thereby produce filtered data and subtracting the filtered data from the spectral data relating to the sample under investigation in order to provide a corrected output data.

11. A method of operating a spectrometer which comprises a source of analyzing radiation, a detector for detecting radiation transmitted through or reflected from a sample under investigation, and a processor for processing the output of the detector to produce spectral data relating to the sample under investigation, said method being carried out in order to suppress the effects of at least one unwanted component in the spectral data, and comprising the steps of acquiring reference data representing high resolution spectra of the at least one unwanted component, modifying said reference data so that its resolution simulates that of the spectrometer, filtering said reference data so as to allow for perturbing effects in the sample spectrum and thereby produce filtered data and subtracting the filtered data from the spectral data relating to the sample under investigation in order to provide a corrected output data, wherein the processor generates perturbed versions of the broadened reference data to take into account variations in at least some operating parameters such as temperature and optical line width.

12. A method of operating a spectrometer which comprises a source of analyzing radiation, a detector for detecting radiation transmitted through or reflected from a sample under investigation, and a processor for processing the output of the detector to produce spectral data relating to the sample under investigation, said method being carried out in order to suppress the effects of at least one unwanted component in the spectral data, and comprising the steps of acquiring reference data representing high resolution spectra of the at least one unwanted component, modifying said reference data so that its resolution simulates that of the spectrometer, filtering said reference data so as to allow for perturbing effects in the sample spectrum and thereby produce filtered data, wherein the filtering step includes creating a filter for filtering the reference data to emphasise the high resolution spectra of the at least one unwanted component, and subtracting the filtered data from the spectral data relating to the sample under investigation in order to provide a corrected output data.

13. A method according to claim 12 wherein the filer comprises a band pass filter.

14. A method according to claim 12 wherein the filtering step also includes carrying out at least square fit of the filtered sample spectral data to the filtered unwanted component spectra.

15. A method according to claim 14 including iterating the least square fit to remove those parts of the spectrum which have a poor fit.

16. A method according to claim 14 including using the resulting co-efficients to compute an unfiltered unwanted component spectrum which is then subtracted form the measured sample spectrum.

\* \* \* \* \*